United States Patent [19]

Ritchey

[11] 4,146,607
[45] Mar. 27, 1979

[54] SYNERGISTIC ANTI-PLAQUE MIXTURE WITH TETRADECYLAMINE PLUS ALUMINUM AND/OR ZINC

[75] Inventor: Thomas W. Ritchey, Norwood, N.J.

[73] Assignee: Lever Brothers Company, New York, N.Y.

[21] Appl. No.: 849,046

[22] Filed: Nov. 7, 1977

[51] Int. Cl.$^2$ .............................................. A61K 7/22
[52] U.S. Cl. ................................... 424/54; 424/145; 424/154; 424/289; 424/325
[58] Field of Search .................................. 424/48–58, 424/145, 154, 289, 325

[56] References Cited

U.S. PATENT DOCUMENTS

| | | | |
|---|---|---|---|
| 2,876,167 | 3/1959 | Manahan | 424/52 |
| 3,083,143 | 3/1963 | Schmid et al. | 424/52 |
| 3,175,951 | 3/1965 | Tucker et al. | 424/52 |
| 3,728,446 | 4/1973 | Roberts et al. | 424/49 |
| 3,772,431 | 11/1973 | Mlkvy et al. | 424/49 X |
| 3,888,976 | 6/1975 | Mlkvy et al. | 424/49 X |
| 3,943,267 | 3/1976 | Randol | 424/49 X |
| 4,022,880 | 5/1977 | Winson et al. | 424/49 |

FOREIGN PATENT DOCUMENTS 1965046 12/1969 Fed. Rep. of Germany .............. 424/52
40-14320 8/1965 Japan ........................................ 424/52

OTHER PUBLICATIONS

Bass et al., J. Dent. Res. 54(5): 968–971, (1975), Quantitative Studies of in Vitro Inhibition of Streptococcus Mutans Plaque Formation by Organic Amines".
Warner et al., J. Dent. Res. 55(1): 130–134, (1976), A Physico Chemical Approach to the Study of Amines as Antiplaque Agents.

*Primary Examiner*—Shep K. Rose
*Attorney, Agent, or Firm*—James J. Farrell; Melvin H. Kurtz; Kenneth F. Dusyn

[57] ABSTRACT

A method and a composition for retarding plaque are disclosed. The composition includes a synergistic mixture of tetradecylamine in combination with aluminum and/or zinc, each of which may be used singly or in admixture in combination with the amine. The method generally includes applying a mixture of the tetradecylamine in combination with one or more of the above metals to the site of the plaque.

7 Claims, No Drawings

SYNERGISTIC ANTI-PLAQUE MIXTURE WITH TETRADECYLAMINE PLUS ALUMINUM AND/OR ZINC

The present invention relates to a novel method and composition for controlling plaque. As a result of the control of plaque, the novel method and composition of this invention may result in an improvement in the control of caries, calculus and general gum health.

Dental plaque forms as a film on teeth. It is a dense microbial layer formed as a product of microbial growth. The closely matted microorganisms in plaque are embedded in a proteinaceous matrix of uncertain origin (but generally considered to be at least partially salivary). The microorganisms involved are mainly coccoidal, this is especially true in early plaque which in the mouths of some persons change to filamentous organisms after a few days. It is generally believed that dental plaque preceeds calculus. Also, it is generally accepted by dental experts that clinical supra-gingival calculus (tartar) is a type of dental plaque which is mineralized with a formation of a calcium phosphate crystalline structure. It will be apparent therefore that the incidence of calculus formation can be reduced by employing dental compositions which reduce or prevent the deposition of plaque. Dental plaque has been observed to form following a dental prophylaxis due to bacteria which are acquired from the saliva where they had resided and remained unaffected by the prophylaxis treatment. Plaque may form on any part of the tooth surface and is found particularly at the gingival margin, and on the surface of dental calculus. The importance of giving consideration to the action of plaque on the teeth is because plaque produces gingivitis and other types of gingival disease as well as dental caries.

Plaque, like calculus, is considered to be a prime causative factor in periodontal disease.

A brief discussion of the pertinent air follows:

Attempts have been made to retard the accumulation of dental plaque by means of aliphatic amines. R. M. King in the *Journal of Dental Research*, Volume 30, June 1951, pages 399–402, describes a clinical study of the effect of tetradecylamine on plaque formation. When present at a level of 1% and compared to a placebo toothpaste, a reduction of nearly 40% in plaque growth is seen for tetradecylamine after a test period of three weeks which includes brushing and normal dental care. Thus, the antiplaque value of tetradecylamine is demonstrated.

Subsequently, U. Herman and H. R. Muhlemann combined the antiplaque properties of the amine with the anticaries action of the fluoride anion, since the amine and the fluoride reduce caries by presumably different mechanisms. Their work, published in 1958, *Helv. Odont. Acta*, Volume 2, page 28, describes the inhibition of salivary respiration and glycolysis by an organic fluoride (aliphatic amine and an equimolar concentration of fluoride). H. R. Muhlemann, H. Schmid, and K. G. Konig also measured enamel solubility which was reduced by the use of inorganic and organic fluorides (*Helv. Odont. Acta*, Vol. 1, p. 23: 1957).

Much of the work on amine fluorides was published in the nineteenth volume of *Helvetica Odontologica Acta*.

The most complete studies of amine fluorides may be found in supplement VIII, April 1974, of *Helv. Odont. Acta*, where the most effective amine fluoride, diethanol amino-propyl-N-ethanol octadecylamine-dihydrofluoride, was reported (T. M. Marthaler, p. 35–44) to reduce caries in a six-year clinical. The antiglycolytic action of amine fluorides, bis-(hydroxyethyl)-amino-propyl-N-hydroxyethyl-octadecylamine-dihydrofluoride, decylamine-hydrofluoride, and sodium fluoride were tested by P. Schneider and H. R. Muhlemann (pp. 63–70), and it was concluded that organic fluorides have an antienzymatic effect which is clearly greater than inorganic fluorides. B. Luscher, B. Regolati and H. R. Muhlemann (pp. 71–78) demonstrated that amine fluorides significantly affects plaque while both amine fluorides and sodium fluoride affects caries.

Work on amine fluorides was based upon the hypothesis that an organic fluoride would be taken up more readily than inorganic fluoride by bacteria to prevent caries. The anticaries action of fluoride is thought to be due to the deposition of fluoride onto the teeth to lower their solubility by acids. The effect on caries from amine fluorides are only additive: amines reduce plaque formation while fluoride reduces enamel solubility.

T. Breitenmoser (*Helv. Odont. Acta*, April 1975, pp. 13–17) compared amine fluorides with amine chlorides for their antiglycolytic action on dental plaque. Breitenmoser demonstrated that amine chlorides were potent antibacterial agents and were no less effective than their corresponding amine fluorides. Thus, the aliphatic amine was the antiplaque ingredient. However, at equimolar concentrations of the fluoride, small antiplaque reductions could be seen.

Several metal cations have been used to aid oral health. Only low concentrations of these metals are necessary to observe clinical effects. U.S. Pat. No. 4,022,880 to Vinson et al, assigned to the assignee hereof and M. Schmid, A. Schait, and H. Muhlemann demonstrated the anticalculus effect of zinc (*Helv. Odont. Acta*, April 1974, Volume 18, pp. 22–24). B. Regolati, A. Schait, R. Schmid and H. Muhlemann demonstrated the anti-caries benefit of titanium and aluminum (*Helv. Odont. Acta*, October 1974, Volume 18, pp. 92–96).

Most metals have some germicidal activity, although metals such as mercury, molybdenum and beryllium are too toxic to be used as antiplaque agents.

J. Sprowls and C. Poe have examined mixtures of four antiseptics, namely phenol, hexylresorcinol, merthiolate, and metaphen, each with several astringent metals, including zinc salts (*J. Amer. Pharm. Assoc.* Vol. XXXII, pp. 33–40, February, 1943). These investigations reported that the germicidal efficiency of the antiseptics was increased by zinc and other metals.

Several patents have been issued which may also be pertinent to the field of oral treatment agents.

U.S. Pat. No. 3,201,316 discloses trifluorostannite salts of amines in oral compositions for caries prophylaxis.

U.S. Pat. No. 2,700,636 discloses dental floss and dental tape impregnated with chemicals for the purpose of increasing the resistance of teeth to deteriorating influences. Zinc chloride or potassium ferrocyanide is disclosed as being one component which may be impregnated in dental floss or dental tape. In addition, other compounds which are disclosed are aliphatic amines, for example tricetylamine as well as many other types of amines, basic inorganic salts, cellulose ether amides and various other compounds. This patent does not disclose any combination of tetradecylamine with a metal, and neither shows nor suggests any synergistic combinations with the metals of this invention.

U.S. Pat. No. 2,333,588 discloses improvements in dentifrices useful for brightening teeth. Fatty amines are disclosed but these amines are not combined with the metals of the instant invention. The patent makes no mention of any synergistic effect on plaque reduction.

U.S. Pat. No. 3,514,513 discloses a dentifrice for hypersensitive dentin utilizing aluminum chlorhydroxy allantoinate. In addition, it discloses that the use of sodium fluoride, sodium silicofluoride, formaldehyde, silver nitrate, zinc chloride and glycerine may be used as components of a dentifrice to treat hypersensitive dentin. This patent does not approach the problem of plaque reduction and does not disclose any aliphatic amines much less the specific tetradecyl amine of the instant invention.

U.S. Pat. Nos. 3,574,859; 3,822,349; 3,839,552 and 3,832,460 disclose a process and composition for the cleaning of teeth and treatment of hypertrophied and hyperplastic gums. Aliphatic amines having 4 to 7 carbon atoms are employed. The patent however does not utilize the tetradecylamine or the metals or metal compounds of the instant invention in a synergistic combination and plaque reduction is not mentioned.

U.S. Pat. No. 3,888,976 discloses a zinc and strontium ion containing effervescent mouthwash tablet. No tetradecylamine is included.

U.S. Pat. No. 3,943,267 discloses treating teeth with a solution of heavy metals such as zinc, iron, chromium, nickel, lead, cobalt, cadmium, copper, platinum, gold and silver to eliminate plaque. No tetradecylamine is mentioned and no synergistic plaque reduction is contemplated.

While the art has approached the problem of plaque reduction from any different standpoints, none of these approaches have been completely satisfactory.

Regular toothbrushing with a conventional abrasive dentifrice may for some persons greatly retard or prevent the accumulation of plaque, for many people however plaque and calculus build-up rapidly even with regular brushing. Thus, an antiplaque system is needed to prevent plaque and safeguard against gingival inflammation, calculus and caries.

Accordingly, an object of the present invention is to provide a new method and compositions for controlling or substantially reducing plaque.

Other objects and advantages will appear as the description proceeds.

The attainment of the above objects is made possible by this invention which includes (1) a composition for controlling plaque comprising: as an active ingredient an antiplaque effective amount of a synergistic mixture containing tetradecylamine in combination with selected metals, the metals preferably being present in substantially soluble form, the tetradecylamine being either soluble or insoluble, and (2) a method for controlling plaque comprising: applying to the site of the plaque, an antiplaque effective amount of a synergistic mixture of tetradecylamine and selected metals, the tetradecylamine and the selected metals being substantially soluble.

The subject invention encompassing novel compositions and methods for the control of plaque overcomes one or more of the disadvantages of the prior art heretofore described. This is accompanied with the advantage that the plaque may be controlled with relatively greater ease while using substantially non-toxic amounts of zinc and/or aluminum with a substantially non-toxic amine.

It has now been discovered that the rate or formation of plaque can be greatly retarded by contacting the site of the plaque with the compositions of the instant invention, specifically tetradecylamine in combination with aluminum and/or zinc. This combination may include one or more toxicologically safe salts which furnish the metallic ion. The tetradecylamine may also be included as a toxicologically safe compound or salt. According to the Seventh Issue of Merck Index aluminum and zinc have an $LD_{50}$ orally in rats of approximately 3–4 g/kg body weight.

The essence of the invention consists, thus, of a synergistic combination with greater antiplaque activity than the simple additive effect of both of the constituent compounds. Tetradecylamine when used alone exhibits good antiplaque activity but when coupled with the selected metals of this invention, gives significant additional activity. In addition to their synergistic activity, the metals were chosen for their solubility, low astringency and low toxicity. Such metals as mercury, beryllium and bismuth may be synergistic with tetradecylamine but may be unsuitable for use in the oral cavity.

While not wishing to be bound by the following theories, it is postulated first that the amine facilitates the penetration of the bacterial cell wall by the germicidal metal. Charged metals are normally excluded from inside microorganisms by a lipid-protein cell wall. The lypophilic tetradecylamine may solubilize the cell wall or mask the charge of the metal to allow passage of the particle into the bacterial cell. An increased death of microorganisms will be manifested in a reduction of plaque growth and its accumulation. Several antibiotics, including the sulfa drugs have been shown to work synergistically with metals. While antibacterial agents alone will kill or retard the growth of plaque bacteria, neither the metal ions nor the tetradecylamine of this invention can easily be used at levels permissible in the oral cavity which produce the technical effect possible with the two in combination. Additionally, as a second postulate, the level of antiplaque activity may be increased because the synergistic combination reduces the surface energy and surface tension of the tooth pellicle. The pellicle may be covered by a low surface tension monolayer of tetradecylamine and positively charged metal ions. In effect, this lower surface tension may reduce the affinity of plaque to the dentition. Further, this monolayer may reduce the incidence of caries by preventing the transport of ions from the enamel surface.

The latter theory, regarding lowering of surface tension, is favored since the antiplaque compositions of the instant invention failed to demonstrate synergistic germicidal activity in bacterial cultures. In addition, the critical micellular concentration (CMC) of tetradecylamine was found to be lowered in combination with selected metals. Bass, Dillingham and Powers (J. Dent. Res. 54: 968–971, (1975)) showed that lowering the CMC in a series of aliphatic amines increased the antiplaque activity. The CMC of other amines was not lowered in combination with zinc. It was found that lowering the CMC paralleled the finding of synergistic plaque reduction of the present invention. Aluminum and/or zinc metals are thought to lower the CMC of tetradecylamine by forming ion pairs. This theory was further confirmed when it was found that the addition of $CO_2$ to tetradecylamine increased antiplaque activity while lowering the CMC. The final evidence was offered when it was found that during formulation, if nonionic detergents such as Brij, Tween or Triton products were employed, the CMC of tetradecylamine in combination with selected metals was raised to that concentration expected for tetradecylamine alone, while the synergistic plaque reductions were lost, leaving plaque reductions indicative of only tetradecylamine.

Dodecylamine, dimethyldodecylamine, hexadecylamine, decylamine, and N,N'-dimethyl-octadecylamine do not give synergistic plaque reductions. Only the primary aliphatic amine with a fourteen carbon chain length acted synergistically with zinc or aluminum.

The minimum amount of the metal compound or mixtures of compounds necessary to result in a control of plaque is generally about 0.001 molar at the site of formation of the plaque. While their is no maximum effective concentration, an amount significantly higher than about 0.05 molar will be difficult to formulate in an organoleptically acceptable mouthwash. The particularly preferred metal concentration is about 0.018 for aluminum and 0.020 molar for zinc in combination with tetradecylamine in a mouthrise for application to plaque. The maximum concentration which can be utilized is properly determined by product parameters such as astringency and formulation compatibilities. The optimum pH of a mouthrinse being about 4.1 for aluminum and 4.3 for zinc to deliver sufficient metal ions to the site of plaque formation.

The concentration of metal containing compound combined with a vehicle and the tetradecylamine to form the compositions of this invention is not critical and may vary within an organoleptically and toxicologically acceptable limit so long as the amount of compound is sufficient to result in the concentration of 0.001 to 0.05 molar at the site of formation of the plaque.

The optimum amount of the tetradecylamine necessary to result in a control of plaque when combined with the metals of the instant invention is generally about 0.005 molar in a rinse. While there is no maximum effective concentration, amounts significantly higher than about 0.05 molar will be difficult to formulate in an organoleptically and toxicologically acceptable mouthwash or manner.

The maximum concentration of tetradecylamine which can be utilized is thus properly determined by product parameters as listed above in relation to the maximum amount of metal which can be used.

Without tetradecylamine the high level of the metal which would be necessary to observe significant benefit is too astringent and/or toxic for normal therapeutic use. Furthermore, high levels of plaque reduction with a metal have never been demonstrated in a clinical study. In addition, high levels of metals are difficult to formulate into a product acceptable to the consumer.

Tetradecylamine without a metal does not attain the desired plaque reductions. While higher levels of this amine confer additional benefit, its bitter taste, greater toxicity, problems of solubility and compatibility with the vehicle provide practical limits of increasing its concentration.

This invention suggests the use of the highest possible level of tetradecylamine which is non-toxic and suitable for formulation. The addition of the metal to the amine does not markedly affect the toxicity or acceptability of the amine. By using the synergistic mixtures of this invention advantage is taken not only of their co-action, but also of the fact that low levels of each can be employed.

In one embodiment, the invention comprises a water-alcohol soluble tetradecylamine/metal mouthwash (oral rinse) which reduces dental plaque. In a further embodiment, the combination of the invention may be used in a dentifrice. The essential components of the invention are an orally acceptable medium, which may be for example, water and alcohol, and the antiplaque mixture. The term "orally acceptable medium" applies to any suitable carrier medium for the antiplaque mixture; such a medium is selected to be harmless to the oral cavity and is not meant to be intentionally swallowed, however the medium is, of course, harmless in an amount accidentally ingested during use.

The compositions of the instant invention may be utilized with a variety of orally compatible agents such as mouthwashes, toothpastes, dentifrices, tooth powders, lozenges, and chewing gum as well as any compatible vehicle for applying the synergistic combination at the specific site of plaque formation. Such formulations being generally prepared in accordance with the art recognized practice.

In mouthwash formulations, for example, the medium includes typically an essentially aqueous solution of alcohol, glycerine or sorbitol. In some mouthwash formulations it is not essential to use any of these materials although they do help to solubilize certain flavor oils. A suitable mouthrinse, for example, contains about 0.02 molar tetradecylamine and about 0.02 molar metal in a medium consisting essentially of 75%–95% water and 5–25% ethanol. Other common additives that do not affect synergism may also be present.

In toothpastes and tooth powder formulations, the essential ingredient other than tetradecylamine and the aluminum and/or zinc compound of this invention is a suitable dental abrasive. It is recommended that the abrasives used in the dentifrice formulation of the present invention provide a final composition which has an acceptable dentin abrasion value. Suitable dental abrasive substances include finely divided particles of appropriate size, hardness and composition for dentifrice abrasives.

Toothpastes and tooth powder formulations also commonly contain a soap or synthetic surface active agent. It is essential in these formulations as well as mouthwash formulations to provide sufficient foaming action to satisfy a market consumer preference for this property. A preferred material for dentifrices is sodium lauryl sulfate. However, many other surface active agents can be used so long as they are compatible, i.e. they do not interfere with the activity of the aluminum compound synergistic combination.

In addition, the toothpaste formulation will frequently contain humectants sufficient to provide smooth texture and flowability. Glycerine and sorbitol are preferred for this purpose together with suitable amounts of water, ethyl alcohol, glucose, and mannitol.

Lastly, the toothpaste formulation generally contains selected binding agents. These also should be compatible with the synergistic combination as well as with the other toothpaste components. For example, cellulose ethers are one type of preferred binder.

A chewing gum medium normally comprises a gum base and common flavoring materials used in the field. The flavoring materials are present at a level of about 0.01–2.0% of the final chewing gum composition. The base is a chewable plastic gum material such as natural rubber, chickle, polyvinyl acetate, ester gum, coumarone resin, and paraffin wax. The gum base is typically made from a mixture of two or more plastic gum materials to achieve a preferred degree of plasticity for chewing. Optionally, a binder or a softener may be used as well as sweetening agents.

Lozenges may be made containing the synergistic combination with a suitable binder.

TEST PROCEDURE FOR DETERMINING ANTIPLAQUE ACTIVITY

The in vitro test used for examining the effects of chemotherapeutic agents on plaque was reported in the *Journal of Dental Research*, Vol. 55, February 1976, page B286, by R. T. Evans, P. J. Baker, R. A. Coburn and R. J. Genco. This assay system for producing artificial plaque was developed to rapidly screen antiplaque agents under conditions which simulate those found in the oral cavity. Evans et al found that effective dosages in the in vitro assay correlated with results of previously published clinical studies. The assay gives reproducible, quantitative results and has the ability to distinguish between antibacterial agents which are clinically effective or non-effective as plaque inhibitors.

The in vitro plaque was formed at 37° C. on uniformly-sized aluminum plummets which were first coated with saliva. The plummets were then placed in a growth medium inoculated with clinical plaque samples. After seven hours the plummets were suspended overnight in a 25% saliva mixture. On the second day, the plummets were immersed in a 50% saliva - 50% test compound mixture for one minute, placed in the growth medium for seven hours, retreated with the test mixture and suspended in 25% saliva overnight. The plummets were treated again on the third day and incubated in the growth medium for three hours. The plaques were removed from the plummets by sonication into approximately six milliliters of buffer and quantitated by optical density (O.D.) in a Beckman DU at 570 mm.

A test compound showed antiplaque activity if the O.D. (plaque mass) was reduced from the control plaques treated with water. Positive controls were included to determine relative activity. Comparisons of antiplaque activity were then made within a given experiment. At least five replicas per compound were examined.

The following Examples will more fully illustrate the embodiments of this invention. All parts and proportions referred to herein and in the appended claims are by weight unless otherwise noted.

EXAMPLE I

The effects of $H_2O$, 0.04% cetyl pyridinium chloride (CPC), 0.060% tetradecylamine (TDA); 0.30% $ZnCl_2$ and several concentrations of zinc plus tetradecylamine are examined, by the artificial plaque method previously described, all with 15% ethanol, at pH 4.1. The results are as follows in Table I.

TABLE I

| Active | % Wt/Vol. | Average Optical Density | Standard Deviation | % Reduction |
|---|---|---|---|---|
| $H_2O$ | — | .704 | .028 | — |
| CPC | .040 | .515 | .014 | 26.9 |
| TDA | .060 | .571 | .035 | 18.8 |
| $ZnCl_2$ | .30 | .766 | .022 | −8.0* |
| $ZnCl_2$ > TDA | .10 / .060 | .451 | .012 | 35.9 |
| $ZnCl_2$ > TDA | .20 / .060 | .436 | .041 | 38.0 |

TABLE I-continued

| Active | % Wt/Vol. | Average Optical Density | Standard Deviation | % Reduction |
|---|---|---|---|---|
| $ZnCl_2$ > TDA | .30 / .060 | .394 | .022 | 44.0 |

*Weight gain

At these metal concentrations, there is often a small increase in plaque weight with the in vitro assay. Clinical data suggest that zinc provides about 5% reduction in plaque.

Tetradecylamine was slightly less effective than the quaternary ammonium germicide, CPC. This level of TDA was selected since it could also be employed in human testing without creating any problems of toxicology. It is clear that the combination of $ZnCl_2$ and tetradecylamine produced a synergistic effect. This is observed in more than seven confirmatory experiments.

The dose-response of tetradecylamine indicates the necessity of increasing the concentration from 0.060% to 0.20% in order to raise the plaque reduction from 18% to 44% when a metal is not present. This higher level would be expected to be more toxic and more bitter than lower levels.

EXAMPLE II

To test higher levels of tetradecylamine, the artificial plaque treatment previously described is eliminated on the third day to simulate infrequent use of the antiplaque product. The results of tetradecylamine in combination with zinc or aluminum are listed in Table II.

TABLE II

| Active | % Wt/Vol. | Average Optical Density | Deviation | % Reduction |
|---|---|---|---|---|
| $H_2O$ | — | 1.113 | .018 | — |
| TDA | .120 | .882 | .076 | 20.7 |
| $AlCl_3 \cdot 6H_2O$ | 1.00 | 1.218 | .026 | −9.4* |
| $AlCl_3 \cdot 6H_2O$ | .250 | 1.080 | .045 | 3.0 |
| $AlCl_3 \cdot 6H_2O$ | 1.00 | .371 | .034 | 66.6 |
| TDA > $AlCl_3 \cdot 6H_2O$ | .120 / .50 | .161 | .012 | 85.5 |
| TDA > $AlCl_3 \cdot 6H_2O$ | .120 / .250 | .150 | .011 | 86.5 |
| TDA $ZnCl_2$ TDA | .120 / .20 / .120 | .456 | .026 | 59.0 |

*Weight gain

The data show that even low amounts of aluminum in combination with tetradecylamine cause the synergistic reduction of plaque. This observation is verified by more than ten individual experiments. When compared with zinc and tetradecylamine, equimolar amounts of aluminum and tetradecylamine give statistically greater reductions. In addition, aluminum is less astringent and may be less toxic, thus, aluminum plus tetradecylamine may be more useful in a therapeutic product.

It is postulated that the weight gains observed with the metals alone are the result of the precipitation of salivary components onto the plummets. Even without regarding these as weight gains, both metal combinations with the amine give wide margins of synergistic reductions over the relatively low reduction seen for the tetradecylamine alone.

Cations such as hydrogen, sodium, potassium, magnesium and calcium, do not give synergistic plaque reductions by the in vitro assay. In addition, synergism is not found with chloride, fluoride, nitrate, phosphate and sulphate.

Two clinical studies are conducted to compare the present invention to another rinse under development which contained 0.04% cetylpyridinium chloride. Although the in vitro test had been shown (Evans et al) to correlate with results of published clinical tests, the amount of synergism in the clinical assays had never been studied. It was decided that two clinicals, each examining a different metal, were necessary to select the mouthrinse with the greatest antiplaque activity, to demonstrate that the aliphatic amine plus zinc or aluminum provide synergistic reductions in dental plaque, to evaluate consumer acceptability, and to look for irritancy by the synergistic combination.

EXAMPLE III

The combination of the metals of the instant invention with tetradecylamine are formulated into several compositions as follows:

|  | A | B | C | D | E | F | G | H |
|---|---|---|---|---|---|---|---|---|
| Alcohol (USP 95%) | 15 | 15 | 15 | 15 | 15 | 15 | 15 | 15 |
| Glycerine | 10 | 10 | 10 | 10 | 10 | 10 | 10 | 10 |
| Sorbitol | 5 | 5 | 5 | 5 | 5 | 5 | 5 | 5 |
| Saccharin | 0.02 | 0.02 | 0.02 | 0.02 | 0.02 | 0.02 | 0.02 | 0.02 |
| $AlCl_3$ | — | — | — | — | — | — | .30 | .30 |
| $ZnCl_2$ | — | — | .20 | — | .20 | — | — | — |
| CPC | — | — | — | .04 | — | .04 | — | — |
| TDA | — | .10 | — | — | .10 | .10 | .10 | — |
| $H_2O$ | balance to 100% | | | | | | | |
| HCl to pH 4.1 | | | | | | | | |

Two studies are conducted. In the first trial sixteen subjects rinse with formulations A, B, C, D, E and F twice daily for five days without brushing. The standard deviations are so large that the only statistically significant difference with 95% confidence is between A, C and B, D, E and F. Zinc chloride, the active ingredient in Lavoris ®, and a positive control for plaque reduction in this experiment tends to increase rather than decrease plaque accumulations. Thus no conclusion about the synergistic activity can be drawn.

A second trial measures plaque growth for thirty hours during which time formulations A, B, D, G and H are used three times. The results show no statistically significant differences among any of the rinses. However the literature abounds with 30–50% reductions with CPC or TDA. Thus no conclusion can be drawn about antiplaque activity from either of the above studies.

No skin irritation was found with TDA in any formulation, and consumer acceptability tended to rank TDA above CPC. During the course of the experiment it was found in vitro that certain ingredients, such as nonionic detergents, inactivate amine plus metal synergism. The effect of these ingredients on synergism was not known.

EXAMPLE IV

The following formulations may be utilized to incorporate the synergistic mixtures of this invention. The specific metal salt used in the formulation is typical of the metal salts which can be used with tetradecylamine (TDA).

| A. Tooth Powder | |
|---|---|
| Abrasive | 90.0 |
| Sodium lauryl sulfate | 3.0 |
| Hydrochloric acid (to pH 3.8) | — |
| $Al_2(SO_4)_3$ | 3.0 |
| Tetradecylamine | 3.0 |
| Flavor | 1.0 |
| | 100.0% |
| B. Toothpaste | |
| Particulate polishing agents | 10.00 |
| Humectant (sorbitol) | 40.00 |
| Sodium lauryl sulfate (21%) glycerine | 7.00 |
| Bodying agent (carboxymethyl cellulose) | 1.00 |
| Flavor, color | 1.5 |
| Zinc | 1.2 |
| Tetradecylamine | 0.3 |
| Hydrochloric acid (to pH 4.4) | — |
| Water | Balance to 100% |

The invention has been described with respect to certain preferred embodiments and various modifications and variations in the light thereof will be suggested to persons skilled in the art and are to be included with the spirit and purview of this application and the scope of the appended claims.

What is claimed is:

1. A substantially non-toxic composition for controlling plaque comprising as an active ingredient an amount of a synergistic mixture of tetradecylamine and a metal wherein said metal is zinc or aluminum or both in admixture with an acceptable oral medium compatible with said mixture, said amount being effective to control said plaque at the site of formation.

2. A composition as defined in claim 1 wherein the amount of said metal is at least about 0.001 molar and of said tetradecylamine is at least about 0.005 molar.

3. A composition as defined in claim 2, said metal being present in an amount of about 0.02 molar and said tetradecylamine being present at about 0.02 molar.

4. A composition as defined in claim 1, said acceptable oral medium comprising water.

5. A method for controlling plaque comprising applying to the site of said plaque, an amount of a synergistic mixture of tetradecylamine and a metal wherein said metal is aluminum or zinc or mixtures thereof, said amount being effective to control said plaque at the site of formation.

6. A method as defined in claim 5 wherein the antiplaque effective amount of said metal is at least about 0.001 molar and the amount of said tetradecylamine is at least about 0.005 molar.

7. A plaque controlling mouthrinse consisting essentially of 0.02 molar tetradecylamine and 0.02 molar metal wherein said metal is zinc or aluminum or both in a medium consisting essentially of 75% to 95% water and 5 to 25% ethanol.

* * * * *